(12) United States Patent
Youssefi

(10) Patent No.: US 6,808,266 B2
(45) Date of Patent: Oct. 26, 2004

(54) OBJECTIVE MANIFEST REFRACTION

(75) Inventor: Gerhard Youssefi, Landshut (DE)

(73) Assignee: Bausch and Lomb, Inc, Rochester, NY (US)

( * ) Notice: Subject to any disclaimer, the term of this patent is extended or adjusted under 35 U.S.C. 154(b) by 156 days.

(21) Appl. No.: 10/100,782

(22) Filed: Mar. 18, 2002

(65) Prior Publication Data

US 2002/0167643 A1 Nov. 14, 2002

Related U.S. Application Data

(60) Provisional application No. 60/284,644, filed on Apr. 18, 2001.

(51) Int. Cl.[7] .............................. A61B 3/00; A61B 3/10
(52) U.S. Cl. ....................................... 351/246; 351/205
(58) Field of Search .................. 351/200, 205–216, 351/221, 222, 246; 600/558; 606/4

(56) References Cited

U.S. PATENT DOCUMENTS

| | | | |
|---|---|---|---|
| 5,777,719 A | | 7/1998 | Williams et al. ............. 351/212 |
| 5,986,760 A | * | 11/1999 | Nakayama et al. ......... 356/511 |
| 6,025,955 A | * | 2/2000 | Hiraiwa et al. ............. 359/355 |
| 6,033,076 A | * | 3/2000 | Braeuning et al. .......... 351/224 |
| 6,095,651 A | | 8/2000 | Williams .................... 351/246 |
| 6,130,419 A | * | 10/2000 | Neal ........................ 250/201.9 |
| 6,181,469 B1 | * | 1/2001 | Hiraiwa et al. ............. 359/355 |
| 6,199,986 B1 | | 3/2001 | Williams .................... 351/221 |
| 6,511,180 B2 | * | 1/2003 | Guirao et al. ............... 351/211 |
| 2003/0007125 A1 | | 1/2003 | Levine | |
| 2003/0007127 A1 | | 1/2003 | Levine | |
| 2003/0189690 A1 | * | 10/2003 | Mihashi et al. ............. 351/221 |

FOREIGN PATENT DOCUMENTS

| | | | | |
|---|---|---|---|---|
| WO | 92 01417 A | 2/1992 | ............ A61B/3/10 |
| WO | 99 27334 A | 6/1999 | ............ G01J/1/00 |

OTHER PUBLICATIONS

Dorsch et al., Accurate computation of mean power and astigmatism by means of Zernike polynomials, Jun. 1998, J. Opt. Soc. Am. A, vol. 15, No. 6, pp. 1686–1688.*

* cited by examiner

Primary Examiner—Brian L. Casler
Assistant Examiner—John R Sanders

(57) ABSTRACT

An method for providing an objective manifest refraction of a patient's eye includes obtaining at least fourth-order Zernike wavefront aberration information, fitting a second-order only polynomial to the at least fourth-order data, and using this information to predict the patient's manifest refraction with an accuracy approaching the patient's subjective manifest refraction. A method is also described for prescribing an accurate vision correction based upon the objective manifest refraction. A display according to the invention includes higher-order wavefront aberrations, lower order wavefront aberrations, numerical indicia of predicted manifest refraction, and images of qualitative assessments of a patient's vision quality. A device for obtaining an objective manifest refraction is described.

14 Claims, 2 Drawing Sheets

OBJECTIVE MANIFEST REFRACTION

This application claims the benefit of Provisional Application No. 60/284,644, filed Apr. 18, 2001.

BACKGROUND OF THE INVENTION

1. Field of the Invention

The invention generally relates to vision diagnostics and, more particularly, to a method for providing improved objective manifest refraction values, an associated method for prescribing a vision correction, and apparatus associated therewith.

2. Description of Related Art

A phoropter is a fundamental optometric diagnostic instrument for vision measurement and evaluation for obtaining a manifest refraction; i.e., defocus and astigmatism (often referred to as "lower-order" aberrations) in an undilated eye. It essentially is a device with a large set of lenses on dials. The device is positioned for a patient to look through and give visual acuity feedback to the practitioner when a particular dialed lens is presented in front of the patient's eye. This method of manifest refractometry provides defocus and astigmatism information to the practitioner typically in order to prescribe vision correcting lenses for the patient. The subjective nature of the phoropter measurement process, from the patient's perspective, is itself a disadvantage of this form of refractometry. Practitioner error can also be problematic, especially when adequate practitioner training may be lacking as it often is in many underdeveloped areas of the world.

An autorefractor is a device that provides an objective diagnostic measurement of a patient's refraction. Although patient subjectivity has been removed from the measurement process, there are other disadvantages associated with autorefractors. First, they are expensive instruments. Second, autorefractor measurements are typically inaccurate, compared to a patient's subjective refraction. There are reports of measurement errors in up to 20% of the population measured in this way. In fact, up to a 2 diopter (D) difference between the objective manifest refraction and subjective manifest refraction has been observed on an individual basis.

A wavefront sensor is a device that measures optical errors in terms of wavefront aberrations. The measured aberrations typically include monochromatic wavefront defects such as spherical aberration, coma, trilateral astigmatism and others, usually referred to as higher-order aberrations. Although wavefront sensing has been used for some time in astronomical and defense applications, the modification, use, and development of this technology in ophthalmology is relatively recent. Moreover, wavefront sensor data is not naturally indicative of manifest refraction. Yet, as vision correction technology advances, wavefront sensing instrumentation will, by necessity, consume office space and resources. Broadening the usefulness of such a tool will justify the costs associated with these instruments.

Based on the foregoing, the inventors have recognized the desirability of being able to accurately predict a manifest refraction based upon objective manifest refraction data, and do it efficiently. Thus, obtaining better measurements with less equipment and less expensive equipment is highly advantageous. The invention also provides an improvement in the ability to specify and prescribe vision correction, including lenses and refractive surgical treatment. Apparatus associated with the invention is further provided. These and other advantages and objects of the invention are described in detail below and with reference to the appended claims.

SUMMARY OF THE INVENTION

The invention, as one of its general objects, is directed to providing an accurate manifest refraction value (referred to herein as "predicted phoropter refraction" or "PPR") from objective measurement data, particularly a wavefront measurement.

In an embodiment of the invention, a method for providing an improved objective manifest refraction includes the steps of objectively obtaining diagnostic measurement data of a patient's eye that is indicative of at least fourth-order Zernike wavefront aberrations or their equivalents, and fitting a second-order only Zernike polynomial to the wavefront data to determine a simplified surface represented by the wavefront information obtained in the preceding step; and for calculating a manifest refraction value from the second-order surface calculation data that accurately corresponds to a subjective manifest refraction value. In various aspects, the wavefront measurement data will preferably include at least fifth and higher-order terms, up to seventh-order terms, and up to tenth-order terms. In an aspect of this embodiment, fitting the second-order Zernike polynomials to the higher-order wavefront data uses a least squares method. The objectively calculated refraction according to the invention (i.e., the predicted phoropter refraction, or PPR) is an accurate rendering of a patient's actual subjective refraction. An accurate PPR is one that is preferably within 0.75D to 0.5D of the patient's subjective refraction; more preferably within 0.5D to 0.25D; and most preferably less than a 0.25D difference from the patient's actual subjective refraction.

A Zernike expansion is a preferred way to describe the aberrations of an optical system. A Seidel aberration model is one of several alternative descriptions of optical aberrations. For more detailed information on this topic the reader is referred to Born and Wolf, *Principles of Optics* (Pergamon, N.Y., 1975), and to Geary, *Introduction to Wavefront Sensors*, SPIE Optical Engineering Press (1995), both of which are incorporated herein by reference in their entirety to the extent allowed by applicable patent rules and laws.

An advantageous offered by the invention is the ability for accurately specifying and prescribing a vision correction for lenses such as spectacle, intra-ocular, and contact lenses, for example, as well as for refractive surgical modification of the cornea, such as LASIK, LASEK, or PRK.

In another embodiment of the invention, a display of an optical diagnostic measurement of a patient's eye, which is typically associated with the measurement apparatus and procedure includes an image representation of second-order and lower aberrations; and an image representation of all measured wavefront aberrations including low-order and higher-order aberrations. In an alternative aspect of this embodiment, the display includes an image representation of an astigmatic wavefront measurement only; and an image representation of third-order and higher wavefront aberrations. Preferably, the displays in both aspects of the embodiment described above will include indicia of the PPR. Preferably, the PPR will be provided for a patient's pupil size of approximately 3 to 4 mm in diameter, and more preferably at a pupil diameter of 3.5 mm. The PPR indicia can optionally be made available for display over a full range of pupil diameters through actual measurement or by appropriate calculations, as understood to those skilled in the art, and incorporated in the hardware or software involved. Moreover, the preferred display will show a vision quality indicator (referred to as a vision metric) such as a Point Spread Function or a Strehl ratio, for example.

BRIEF DESCRIPTION OF THE DRAWINGS

Features and advantages of the present invention will become apparent to those skilled in the art from the following description with reference to the drawings, in which.

DETAILED DESCRIPTION OF PREFERRED EMBODIMENTS OF THE INVENTION

Figure 1:
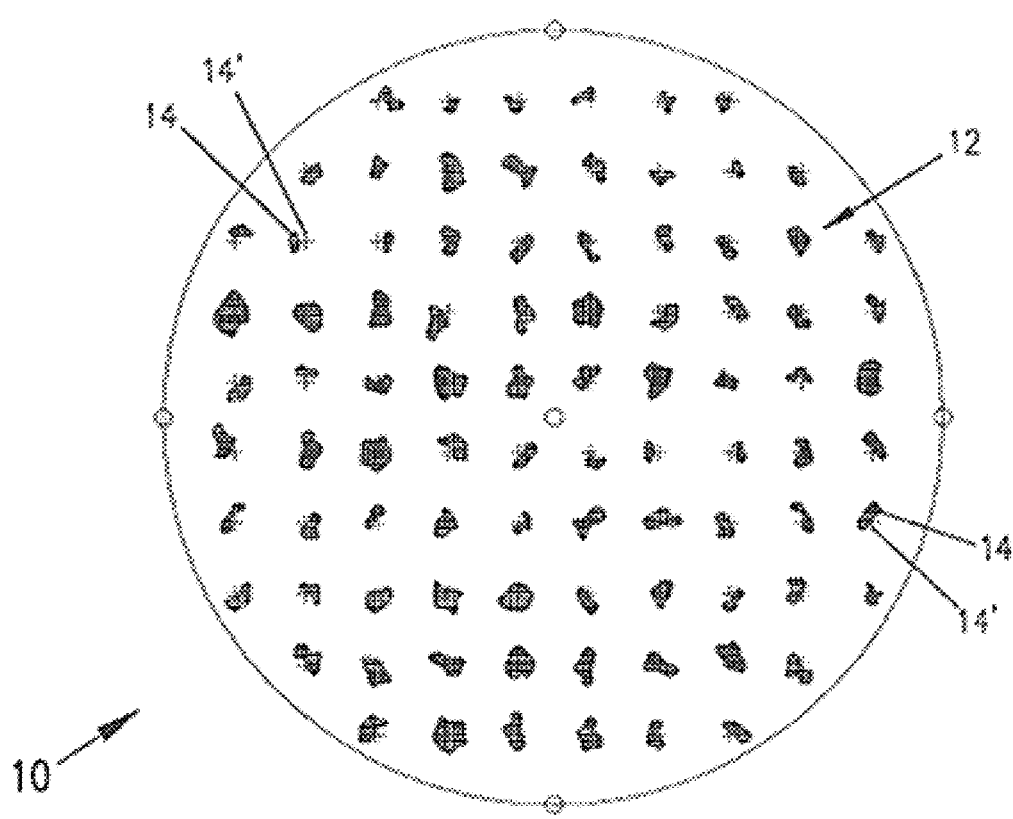
FIG. 1 is an illustrative display of the aerial images of point sources provided by a Hartmann-Shack type wavefront analyzer.

An embodiment of the present invention is an improved method for providing an accurate manifest refraction value from an objective measurement procedure, preferably a wavefront measurement, which is not traditionally associated with providing manifest refraction values.

The measurement error (i.e., deviation from a subjective measurement value) commonly observed in autorefractor measurements is believed by some to be due at least in part to the presence of higher-order aberrations in the eye; i.e., optical error versus refractive (corneal) error. Without limitation to the invention described and claimed herein, this can be thought of as follows: optical aberrations such as, but not limited to, defocus, astigmatism, spherical aberration, and coma are described mathematically, for example, by Zernike polynomials and by other mathematical expressions. The Zernike polynomial equations include second-order, third-order, fourth-order, fifth-order, etc. terms wherein the second-order and lower terms describe the defocus and astigmatism errors (also known as sphere and cylinder, respectively) while the third-order and higher terms describe higher-order aberrations such as spherical aberration, irregular astigmatism, coma, and others. While defocus, the aberration typically measured by traditional subjective and objective refractometry, is a second-order optical aberration, a finite contribution from defocus shows up in the mathematical description of, e.g., fourth-order spherical aberration. Therefore, the typical algorithms used by traditional auto-refractometry devices that do not account for the higher-order contributions of refractive error provide at best only an estimate of defocus and astigmatism. This is exemplified by the difference between the objective refraction provided by the autorefractor and the actual prescription of the lenses preferred by the patient (subjective refraction) for comfortable vision.

In a preferred embodiment, an objective, diagnostic wavefront measurement of a patient's eye is obtained by a practitioner, preferably by using a wavefront sensor device. Wavefront sensing is used to directly measure the wavefront aberrations produced by a patient's eye. This technology and an associated device are illustratively described, for example, in Williams U.S. Pat. No. 5,777,719, and is commercially embodied in the Zywave™ wavefront analyzer manufactured by Bausch & Lomb/Technolas (Rochester, N.Y./Munich, Germany). The Zywave uses a Hartmann-Shack wavefront sensor that utilizes a lenslet array to measure and compute higher-order aberrations. Depending upon the lenslet array parameters, wavefront aberrations up to tenth order can be measured. Preferably, the patient's eye is not dilated and measurement is made with the pupil diameter in the range of about 3 to 4 mm, however, lighting conditions and other factors may affect pupil size, making the pupil larger or smaller. In any event, diagnostic data can be scaled to be representative of a nominal pupil diameter of about 3.5 mm, which is more preferred to reduce the effects of spherical aberration in the periphery of the optical zone.

With reference to FIG. 1 which shows a display 10 of aerial images 12 produced by the lenslet array of a Hartmann-Shack wavefront sensor, the Hartmann-Shack wavefront sensor output produces signals related to the positional deviation ($\Delta x$, $\Delta y$) of the centroids 14 of the aerial images 12 from their ideal locations (i.e., centroid locations for a non-aberrated wavefront). Because an aberrated wavefront is not planar, each measurement position can be represented by a slope of the wavefront profile at that point; in other words, a dx, dy value. The positional errors $\Delta x$, $\Delta y$ are related to the wavefront slopes dx, dy at each centroid location by equations as follows:

$$\Delta x = \kappa f \frac{dx}{dW} \text{ and}$$

$$\Delta y = \kappa f \frac{dy}{dW}$$

where $\kappa$ is a constant, f is the focal length of the lenslet array and dx/dW, dy/dW are the slope values of the total wavefront at the selected position. The wavefront, represented by a three-dimensional surface, can be calculated by assuming a model for the aberrations, preferably a Zernike model. A Siedel model or other aberration model could also be used as one skilled in the art will appreciate. The Zernike model preferably represents second-order to seventh-order terms, but can vary in the upper limit depending upon lenslet spacing and other sensor parameters. A second-order Zernike model provides defocus and astigmatism data while the third to seventh-order models are indicative of higher-order aberration data. For a more detailed description, the reader is referred to Dorsch et al., Accurate computation of mean power and astigmatism by means of Zernike polynomials, J. Opt. Soc. Am. A/Vol. 15, Mo. 6 (June 1998); Dai, Gung-Ming, Theoretical Studies and Computer Simulations of Post-Detection Atmospheric Turbulence Compensation, Ph.D. thesis, Lund University, Lund Sweden (1995); Wang, J. Y. and Silva, D. E., Wavefront Interpretation with Zernike Polynomials, *Applied Optics*, 9,1510–1518 (1980); and Mahajan, V. N., Zernike Circle Polynomials and Optical Aberrations of Systems with Circular Pupils, *Engineering & Laboratory Notes*, August 1994, S21–S24.

In an embodiment of the invention directed to providing an objective manifest refraction value, a second-order only Zernike model is chosen to fit the higher-order wavefront data for a certain pupil diameter, d, ultimately resulting in the Zernike amplitudes $Z_{200}$, $Z_{220}$, $Z_{221}$ (or their equivalents which are representative of defocus and astigmatism (magnitude and axis), respectively) where $Z_{200}=(sp+cy/2)*10^{6}*r^{2}/(4*\text{sqrt}(3))$;

$Z_{220}=-cy*10^{6}*r^{2}*\cos(2*\text{phi})/(4*\text{sqrt}(6))$; and $Z_{221}=-cy*10^{6}*r^{2}*\sin(2*\text{phi})/(4*\text{sqrt}(6))$ where the Zernike coefficients are given in $\mu$m, the radius r is half the diameter of the pupil in meters, sp is the sphere in diopters, cy is the cylinder in diopters, and phi is the axis of the cylinder in degrees. Notice, that the cylinder is always negative. The Zernike amplitudes provide optical path difference measurements in microns that are converted to diopter values for ophthalmic application. Equivalently, the conversion from the second-order Zernike amplitudes to manifest refraction values is realized as follows:

$$\text{Cylinder} \propto 2\sqrt{6}\sqrt{(A^2_{220}+A^2_{221})}\,(2/R^2),$$

$$\text{Axis} \propto \tan^{-1}(-A_{221}/A_{220})\,180/2\pi;\text{ and}$$

$$\text{Sphere} \propto (2\sqrt{3})\,A_{220}(2/R^2)-\text{Cylinder}/2,$$

Where R is pupil radius in mm, A is a Zernike coefficient in $\mu$m.

According to the invention, the defocus (sphere), astigmatism (cylinder) and astigmatic axis measurements are computed using second-order only Zernike terms since these terms themselves represent only second-order aberrations. The PPR is considered accurate if the value is within 0.75D to 0.5D of the patient's actual subjective refraction. More preferably, the PPR will be within 0.5D to 0.25D, and most preferably better than 0.25D of the actual subjective refraction absent a perfect match.

It will be appreciated by a person skilled in the art that other mathematical analyses can be used to provide the ultimate coefficient values for defocus and astigmatism representations of the manifest refraction values. In any event, it is solely the second order contribution that is being used to describe the higher order contributions of the wavefront.

Other wavefront sensing techniques and devices known to those skilled in the art can likewise be used to obtain the appropriate diagnostic wavefront information and, as such, the invention is not limited to Hartmann-Shack data. In fact, sufficient data may be obtainable from ray tracing information obtained by topography and other methods. Moreover, it will be understood that the step of obtaining the diagnostic wavefront measurement need not require the contemporaneous making of a wavefront measurement; rather, for the invention one need obtain only the appropriate description of the wavefront surface, preferably in the form of Zernike data, to which a second-order curve can be fit. Therefore, a previously acquired and stored measurement, a remotely acquired and transmitted measurement, a contemporaneous measurement, etc. can supply the necessary data according to the invention.

In an aspect of this embodiment, a method for selecting/describing and/or providing a vision correction prescription includes obtaining the PPR information as described above, and using this information to prescribe a correcting spectacle lens, for instance, for the patient. Since traditional spectacle and contact lenses, for example, only correct a patient's vision for defocus and astigmatism, and typically not higher-order aberrations, an accurate manifest refraction is key to providing the best performing lens or vision correcting procedure for the patient.

Figure 2:
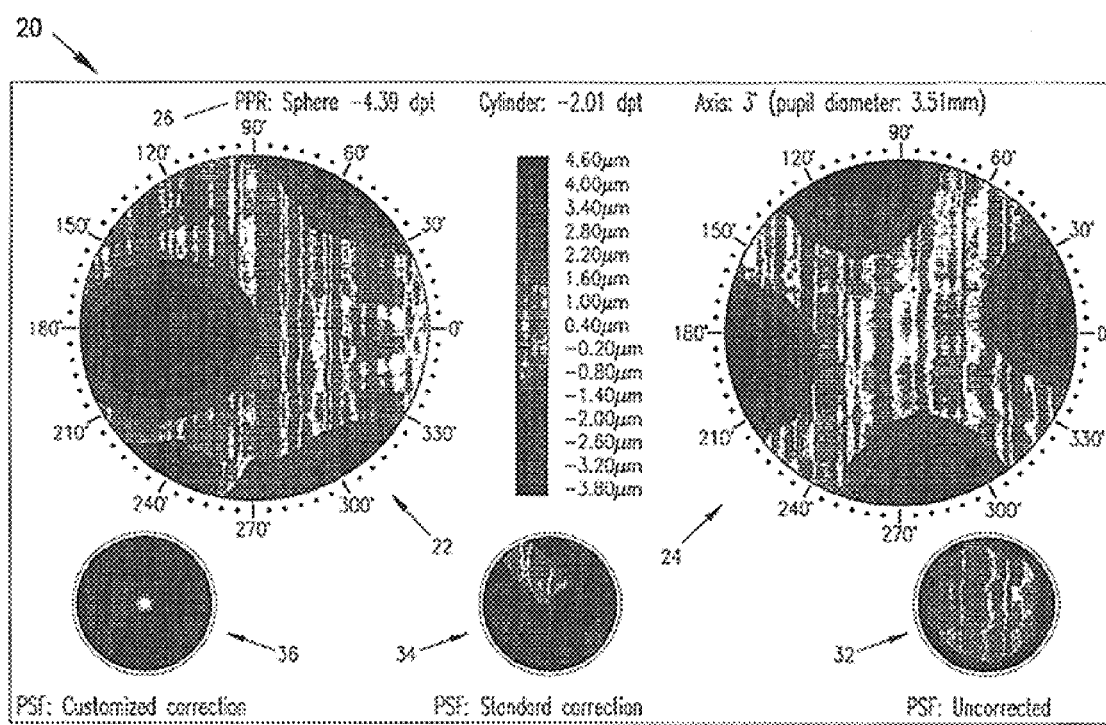
FIG. 2 is an exemplary display of an optical diagnostic measurement of a patient's eye according to an embodiment of the invention.

In another embodiment of the invention, a display 20 of information is illustrated in FIG. 2. As shown, there is a wavefront map 22 of the patient's lower-order (second-order and lower) aberrations and a wavefront map 24 of the patient's higher-order (third-order and higher) aberrations. The picture of the lower-order aberration 22 may show only defocus, only astigmatism, or defocus and astigmatism. The display 20 also shows the predicted phoropter refraction (PPR) value 26 calculated as described above. The display preferably also shows an image representation of a point spread function (PSF) corresponding to the uncorrected state of the patient's eye 32, an image representation of a PSF corresponding to a standard (lower-order) correction state 34, and a PSF corresponding to a customized (best corrected) correction state of the patient's eye 36. As such, this is a vision quality metric. The Point Spread Function is computed as the squared amplitude of the Fourier transform of the generalized pupil function of the displayed wave aberration function. The maximum value of this function is given along with the maximum value of the PSF of a plane wave for the current "effective" pupil diameter. The ratio of these values, called the Strehl ratio, can also be displayed. The Strehl ratio can also be used as an image (or vision) quality index (the closer to 1, the better the image). Preferably, the displayed PSF function is only the central 1/16 of the full function in order that some detail may be seen. Generally, the maximum value occurs is this region.

While various advantageous embodiments have been chosen to illustrate the invention, it will be understood by those skilled in the art that various changes and modifications can be made therein without departing from the scope of the invention as defined in the appended claims.

I claim:

1. A method for objectively obtaining a refraction value of a patient's eye, comprising:

objectively obtaining a diagnostic measurement data of a patient's eye that is indicative of at least fourth-order Zernike wavefront aberrations or their equivalents;

fitting a second-order only polynomial to the wavefront data to describe the aberrated wave front; and calculating a manifest refraction value from the second-order polynomial fit.

2. The method of claim 1, further comprising displaying a value for the calculated manifest refraction.

3. The method of claim 1, further comprising calculating a vision assessment metric.

4. The method of claim 3 wherein said vision assessment metric comprises at least one of a point spread function (PSF) value, a line spread function (LSF) value, and a Strehl ratio.

5. The method of claim 4, wherein said calculating step comprises calculating the respective value corresponding to the patient's wavefront aberrations in at least one of an uncorrected state, a standard correction (lower-order) state, and in a custom corrected (best corrected) state.

6. The method of claim 5, further comprising displaying an image representation of the calculated values.

7. The method of claim 1, wherein obtaining the diagnostic measurement data comprises making a contemporaneous wavefront measurement.

8. The method of claim 1, wherein obtaining the diagnostic measurement data comprises using stored data.

9. The method of claim 1, wherein obtaining the diagnostic measurement data comprises using remotely acquired data that is transmitted to the practitioner.

10. An improved method for determining a vision correcting prescription, comprising:

making an objective diagnostic measurement of a patient's vision that is indicative of at least fourth-order Zernike wavefront aberrations or their equivalent;

fitting a second-order only polynomial to the at least fourth-order data to describe the aberrated wave front;

calculating a manifest refraction value from the second-order polynomial fit; and prescribing a vision correction based upon the calculated manifest refraction.

11. The method of claim 10, comprising prescribing the vision correction for one of a vision correcting lens, an IOL, an inlay, an onlay, and a corneal ablation.

12. The method of claim 10, wherein making the diagnostic measurement includes making a wavefront measurement.

13. A device for measuring an objective manifest refraction of a patient's eye, comprising:

a diagnostic component adapted to measure at least fourth-order Zernike wavefront aberration data or its equivalent;

a calculating component for fitting only a second-order polynomial to the wavefront aberration data and calculating the manifest refraction; and a display component for displaying the calculated manifest refraction.

14. The device of claim 13, wherein the diagnostic component is a wavefront sensor.

* * * * *

UNITED STATES PATENT AND TRADEMARK OFFICE
CERTIFICATE OF CORRECTION

PATENT NO. : 6,808,266 B2
DATED : October 26, 2004
INVENTOR(S) : Gerhard Youssefi It is certified that error appears in the above-identified patent and that said Letters Patent is hereby corrected as shown below:

Column 6,
Line 32, replace "Strehi" with -- Strehl --
Line 55, replace "wave front" with -- wavefront --

Signed and Sealed this

Nineteenth Day of July, 2005

JON W. DUDAS
*Director of the United States Patent and Trademark Office*